United States Patent [19] Jinks et al.

[11] 4,145,928
[45] Mar. 27, 1979

[54] AUTOMATED ENTRAINMENT ABUNDANCE SAMPLER

[75] Inventors: Steven M. Jinks, Middletown; Bruce Muchmore, Tuxedo; Dan Ostrye, Goshen, all of N.Y.

[73] Assignee: Ecological Analysts Inc., Middletown, N.Y.

[21] Appl. No.: 878,358

[22] Filed: Feb. 16, 1978

[51] Int. Cl.² ............................................. G01N 1/14
[52] U.S. Cl. ................................. 73/421 R; 210/262; 210/411; 210/433 R
[58] Field of Search ......... 73/421 R; 210/262, 433 R, 210/411

[56] References Cited
U.S. PATENT DOCUMENTS

| | | | |
|---|---|---|---|
| 1,191,741 | 7/1916 | Scull | 210/172 |
| 1,780,774 | 11/1930 | White | 210/304 |
| 2,066,479 | 1/1937 | MacIsaac | 210/75 |
| 2,732,946 | 1/1956 | Schaub | 210/459 |
| 3,310,984 | 3/1967 | Swanson | 73/431 R |
| 3,879,286 | 4/1975 | Berriman | 210/23 |

Primary Examiner—Richard C. Queisser
Assistant Examiner—Joseph W. Roskos
Attorney, Agent, or Firm—Jones, Tullar & Cooper

[57] ABSTRACT

An automated entrainment abundance sampler for the collection of ichthyoplankton specimens and its operation is disclosed. An inverted conical screen or net is utilized to collect specimens from water supplied by a suitable pump. After a set time period, the collected specimens are further concentrated in a secondary concentrator and transferred to a sample container. The conical screen is rinsed to insure that all the specimens are transferred to the secondary collector which is, in turn, rinsed to further insure that all the specimens are carried to the sample container. A suitable control system is provided to allow the sampler system to operate automaticaly in the collection of specimens over a preselected period of time.

15 Claims, 4 Drawing Figures

AUTOMATED ENTRAINMENT ABUNDANCE SAMPLER

FIELD OF THE INVENTION

The present invention is directed generally to a sampling system for planktonic organisms including the early life stages of fish. More specifically, the present invention is directed to such a sampling system which utilizes an inverted conical filter or net. Most particularly, the present invention is directed to such a sampling system wherein the system can be automatically operated and collects samples almost continuously.

A stream of liquid from which ichthyoplankton specimens are to be collected is fed to the interior of an inverted conical net placed within a tank. The specimens are retained within the net while the liquid passes through and out of the tank. After a selected time interval, the inlet flow of liquid is halted and the specimens and liquid within the cone are drained to a secondary concentrator. The conical net is washed down to insure removal of all the specimens to the secondary concentrator which is, in turn, washed down into a suitable sample container. Suitable controls are provided for the various pumps and valves which control the direction and flow of the specimens and liquid.

DESCRIPTION OF THE PRIOR ART

The separation of solids entrained in a liquid or slurry by the use of suitable filtration equipment is well known in the art. Various sizes of filters and holders, as well as pumps and suitable flow conduits, have been used in a number of filtering of applications. These prior devices, however, are not suited for use in the separation and collection of specimens of ichthyoplankton such as the early life stages of fish where it is necessary to obtain information as to the number of specimens to be found in a certain volume of water. General purpose or industrial filtering systems are not suited for such usage and destroy the specimens during the separation process so that an accurate counting of the specimens is not possible.

The use of various fine nets and the like to secure samples of fish eggs, larvae and juveniles has also been attempted but these have not been satisfactory for several reasons. As with other attempted collection systems, the nets do not provide an accurate sampling because of difficulties in separating the organisms to be sampled and counted from the net without losing or destroying the ichthyoplankton, the inability to accurately measure flow rates of the water being filtered, the inability to rapidly remove the specimens from the device and the general lack of control over the sampling.

Prior systems for the collection of ichthyoplankton specimens have not included a control capability wherein the sampling or collecting can be controlled as a function of time. Prior collections have required the attendance of an operator to control the flow of the specimen bearing liquid and to separate the specimens collected from the collection net or screen. Prior collection devices have also not included suitable means to backwash the filters or screens to insure that all of the specimens being collected were transferred from the collecting screen or net to the sample container.

SUMMARY OF THE INVENTION

It is an object of the present invention to provide an automated entrainment abundance sampler.

Another object of the present invention is to provide an automated abundance sampler wherein the specimens are not harmed or destroyed.

Yet another object of the present invention is to provide an automated abundance sampler in which all of the specimens collected are transferred to a sample container.

A further object of the present invention is to provide an automated entrainment abundance sampler which collects almost continuously.

Still a further object of the present invention is to provide an automated abundance sampler which operates automatically, is portable and includes means for accurately controlling the operation of the sampler assembly.

As will be set forth in greater detail in the description of a preferred embodiment, the automated entrainment abundance sampler in accordance with the present invention includes an inverted conical collection net placed within a vessel and having means for supplying the liquid to be sampled to the interior of the cone. An overflow stand pipe is utilized to maintain a liquid level in the vessel and suitable valves and pumps are provided. After a selected sampling time, the sample inflow is halted and the contents of the net are transferred to a secondary concentrator. The conical net is washed down to insure complete transfer of the specimens to the secondary collector which is, in turn, washed down to a sample container provided with a screened overflow.

The automated entrainment abundance sampler in accordance with the present invention is superior to prior methods and devices used for the collection of ichthyoplankton specimens for several reasons. The system collects almost continuously, thereby integrating the normally large temporal variations in the concentrations of organisms occurring in the field. Samples are drained from the filtering cone and composited into a collecting vessel at regular intervals which are variable from 5 minutes to 3 hours. This procedure minimizes the length of exposure to turbulence in the filtering cone, thereby minimizing possible mechanical damage to the organisms.

During the draining procedure, the filtering cone, secondary concentrator and all piping are spray washed to assure complete transfer of organisms to the collecting vessel. The filtering cone is also specifically structured to provide minimum damage to the organisms, while also minimizing the size of the receiving system required.

The sample storage container may be refrigerated and de-oxygenated. This prevents possible biases from predation and/or decomposition of organisms during the sampling period. (Fish larvae can disintegrate completely in a matter of hours when water temperatures are high.)

The entire system operates automatically according to preset cycle times and intervals over which the sample is to be composited. For example, the system can pump continuously for 30 minutes, drain the organisms from the filtering cone into the collecting vessel and repeat this cycle 48 times to obtain a 24-hour composite sample. Further flexibility is provided by an automated specimen receiving container changer, allowing up to 8 separate composites to be taken automatically. This may be used to automatically sample the diurnal variations in organisms densities, or could be used when long-term unmanned operation is required; i.e., 24-hour composites for up to 8 days.

Other features of the system include accurate water volume measurement by use of a flow meter, cycle and batch counters, self-contained power supply, and portability.

As discussed above, the automated entrainment abundance sampler in accordance with the present invention is primarily intended for use in collecting, compositing and temporarily preserving ichthyoplankton specimens such as the early life stages of fish; i.e., eggs, larvae, and juveniles. The system is especially well suited for sampling programs designed to determine the numbers of organisms being withdrawn from a waterbody by manufacturing or other installations such as cooling water systems of electric power plants.

BRIEF DESCRIPTION OF THE DRAWINGS

While the novel features of the present invention are set forth with particularity in the appended claims, a full and complete understanding of the invention may be had from the detailed description of a preferred embodiment as set forth hereinafter, and as shown in the accompanying drawings in which:

DESCRIPTION OF A PREFERRED EMBODIMENT

Figure 1:
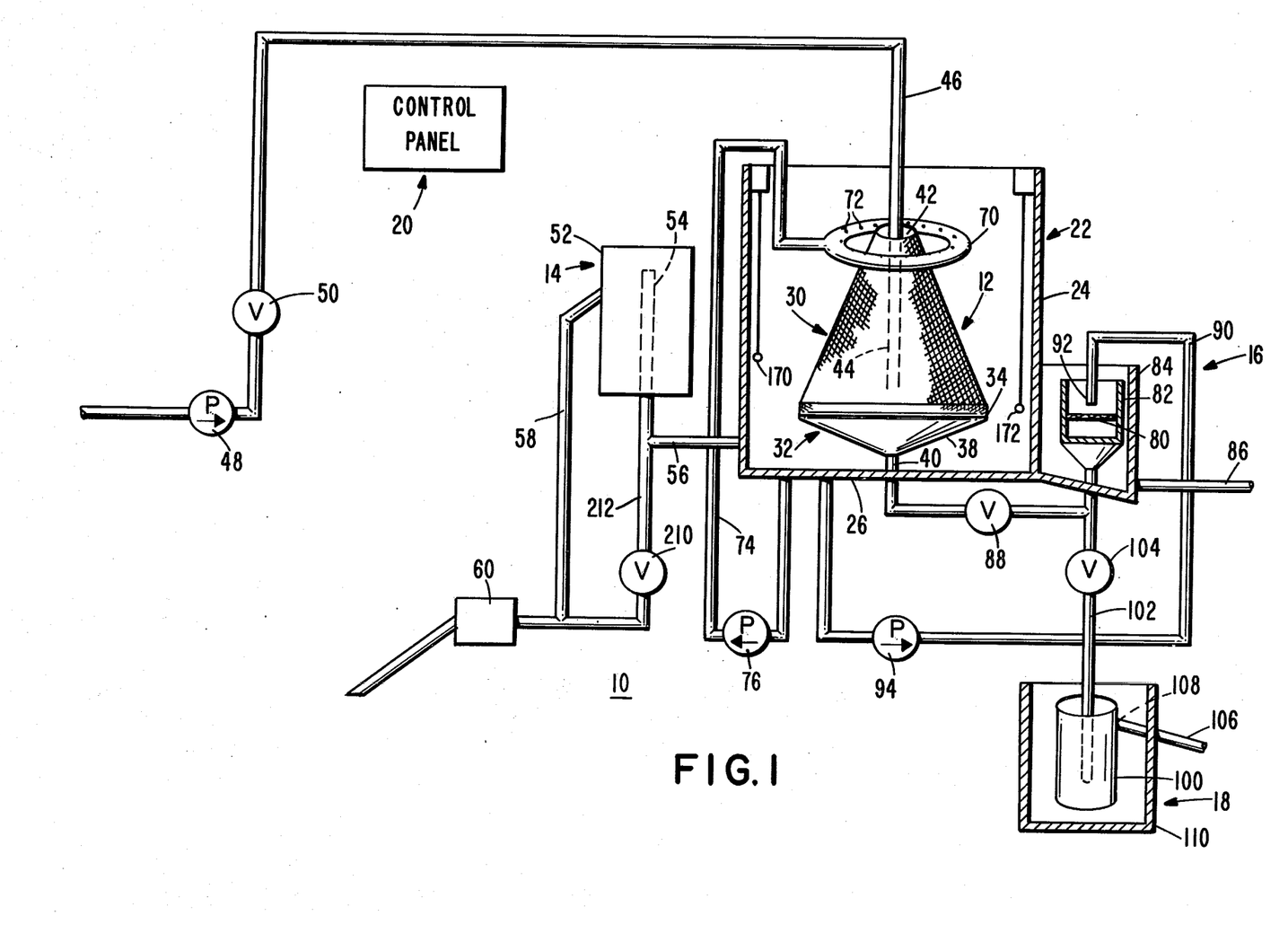
FIG. 1 is a schematic view, partly in section, of an automated entrainment abundance sampler in accordance with the present invention.

Turning now to FIG. 1, there is illustrated, generally at 10, a preferred embodiment of an automated entrainment abundance sampler system in accordance with the present invention. The sampler system is comprised generally of a collection net and funnel generally at 12, a level control and drainage system 14, a secondary concentrator 16, a sample storage system 18, and an automatic controller 20. It will be understood that the orientation of the various components of system 10 need not be as set forth in FIG. 1 which is intended as a schematic representation of the automated entrainment abundance sampler, and that the various portions could be oriented in a wide variety of locations. The system can be either a static installation or can be provided with a suitable housing and the like so that it is transportable to various field locations. The system is also intended to be self-contained and may include whatever batteries or other power supply means which may be required for field operation.

Figure 2:
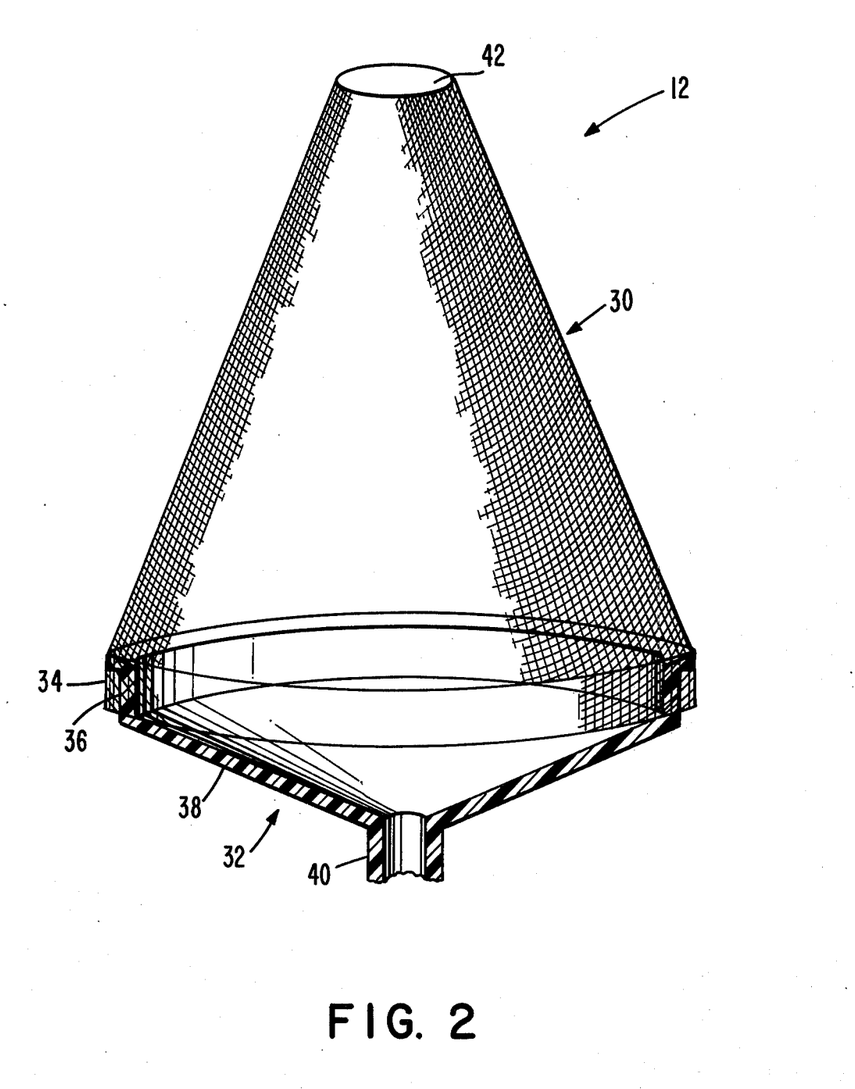
FIG. 2 is a side elevation view, partly in section of an inverted conical collection net and its associated funnel in accordance with the present invention.

Again referring to FIG. 1, the collection net and funnel assembly 12 are shown as being contained within a polyethylene collection tank 22 which includes generally vertical side walls 24 and a bottom 26. The shape and size of tank 22 are variable so long as the tank has sufficient volume to fully enclose the net and funnel 12. Net and funnel assembly 12, illustrated in greater detail in FIG. 2, includes an inverted, conical net 30 of nylon or similar material of 500 micron screen. While nylon is a preferred material for the net 30, it will be understood that any other material which is inert and which will not be affected by repeated contact with water, either fresh or saline, and chemicals and the like which may be carried by the water would be suitable for use as net 30. Similarly, the equipment used throughout the system to be described hereinafter is preferably of inert plastics and the like although any material which will not affect or be affected by the liquid and ichthyoplankton being sampled will be suitable for use. Filter net 30 is positioned over a large diameter, polyethylene collection funnel 32 with a base portion 34 of net 30 being secured by suitable clamp means or the like (not shown) to an upstanding wall portion 36 of funnel 32. The funnel is also provided with sloping side walls 38 which terminate in a funnel drain line 40. The funnel net 30 extends upwardly and inwardly from its base 34 to an open apex 42 which surrounds the discharge end 44 of a sample inlet pipe 46.

Referring again to FIG. 1, sample inlet pipe 46 is provided with a suitable sampling pump 48 and a manually controlled throttle valve 50. In the preferred embodiment, the sample pump 48 is a 3-inch discharge, self-priming, electrically driven, trash pump of open impellor design which is capable of pumping large volumes of water with a minimum of damage to the ichthyoplankton contained in the water. Throttle valve 50 is manually operable to control the volume of water pumped into the collection tank 22.

The level of water in the collection tank 22 is maintained by an overflow tank 52 which includes an overflow sand pipe 54. Overflow tank 52 receives water from tank 22 through an overflow line 56. An overflow tank discharge line 58 carries water away from an upper portion of the overflow tank and through a flowmeter 60 which records the volume flow of water through the system during the sampling cycle. Flowmeter 60 can be of any conventional type and can include suitable recording means (not shown) to keep a record of the liquid flow.

A filter net rinse ring 70 is positioned in collection tank 22 and surrounds an upper portion of filter net 30. Rinse ring 70 is provided with a plurality of nozzles of apertures 72 which can direct a spray of water against the filter net 30 to wash down organisms impinged on the filter or collection net 30 after a sampling cycle has been completed. Liquid is supplied to rinse ring 70 through a rinse ring pipe 74 and a rinse ring pump 76 is provided in the rinse ring piping 74 to draw the water from collection tank 22 and force it out through the rinse ring 70. The sequence of operation of this pump and the several other valves and pumps to be discussed hereinafter will be set forth in greater detail in a subsequent section of the description of a preferred embodiment.

As also illustrated in FIG. 1, the secondary concentrator 16 is comprised of a secondary screen 80 of 500 micron mesh secured within a secondary collection funnel 82 which is, in turn, located within a secondary collection tank 84 having a drain line 86. The collection funnel drain line 40 from the collection funnel 32 passes out through the bottom 26 of tank 22 and upward into the secondary collection funnel 82 below the secondary screen 80. An electrically actuated funnel drain line valve 88 is provided in funnel drain line 40. A secondary screen rinse line 90 extends from tank 22 into the secondary collection tank 84 and terminates in a secondary rinse nozzle 92 which extends into the secondary collection funnel 82 and terminates above secondary screen 80. A secondary rinse pump 94 is located in the secondary screen rinse line 90 and pumps water from the collection tank 22 to the secondary collection screen 80 to wash particles off the secondary screen 80.

Sample storage system 18, as shown schematically in FIG. 1, includes a sample or specimen receiving container 100 into which the sample from the secondary collection funnel 82 is transferred by way of a specimen transfer pipe 102 which extends from the secondary collection funnel. An electrically actuated specimen transfer pipe valve 104 is positioned in the specimen transfer pipe 102 at a point between the secondary collection funnel 82 and the specimen receiving container 100. The container 100 is provieed with a suitable drain line 106 which also contains a 500 micron screen 108. The specimen container 100 is contained within a closed, refrigerated housing 110 which may also be de-oxygenated to prevent decay or bacterial decomposition of the sample or samples. While not specifically shown, it will be understood that a plurality of sample or specimen containers 100 could be movably placed within a suitable refrigerated and deoxygenated housing 110. In this manner, it would be possible to take a number of samples over a certain period of time. Any suitable means such as a revolving sample container holder or a flexible specimen transfer line with suitable indexing means could be used to enable the sample storage system 18 to automatically collect and store various samples over a period of time.

Figure 3:
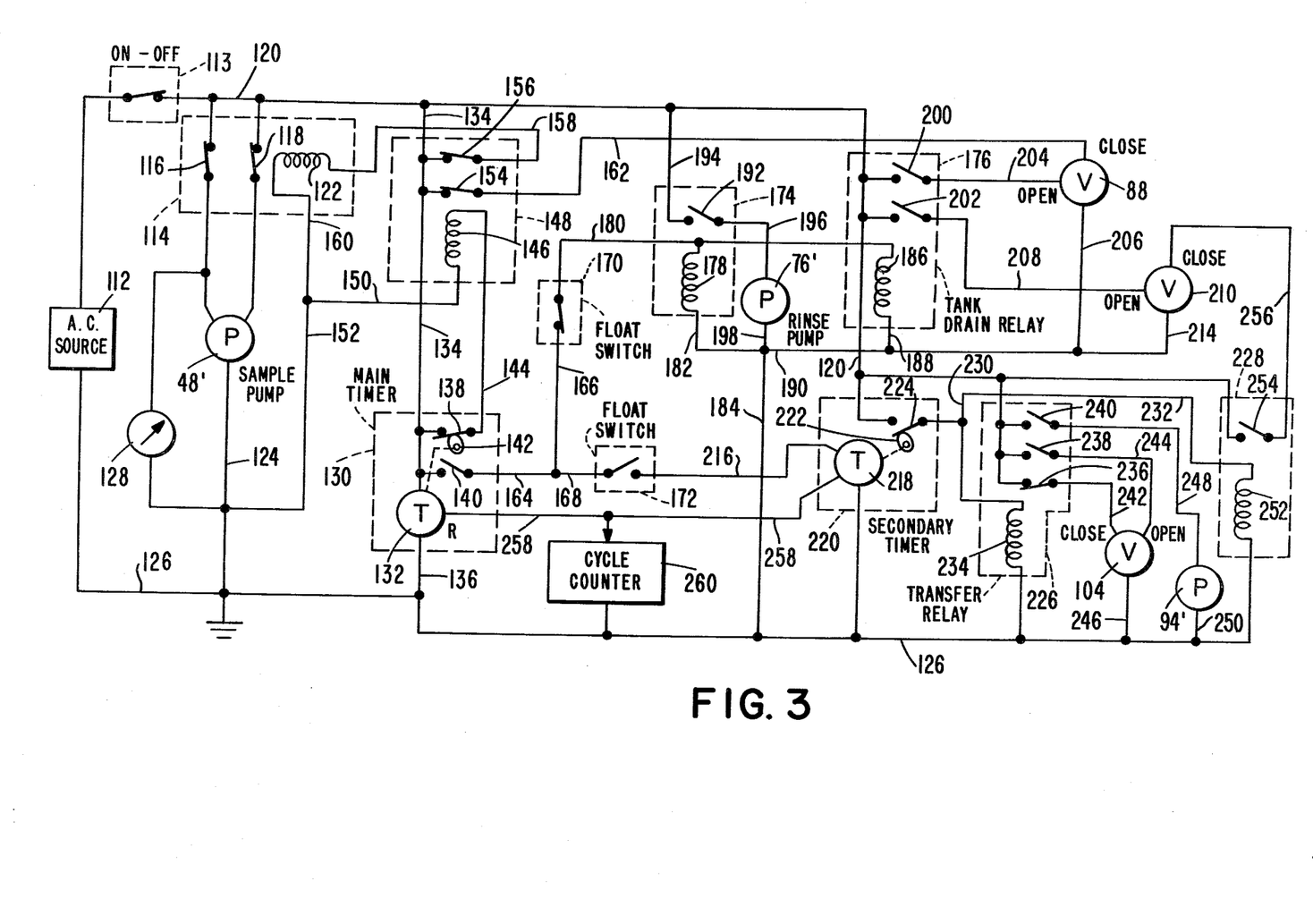
FIG. 3 is a schematic diagram of an automatic control system for the sampler of claim 1.

The controller 20, shows diagrammatically in FIG. 1, is illustrated in greater detail in FIG. 3, to which reference is now made. The control system is shown as being operated from an AC source 112 through a suitable on-off switch 113. Although an AC supply is preferred, it will be evident that by suitable modification on the circuit, including the various motors and valves, DC power may be used to operate the system.

The main sampling pump 48 for the abundance sampler is driven by a corresponding motor 48' which is connected across the AC source through a pump starter relay 114. This relay includes two parallel contacts 116 and 118 connected to AC line 120 and operable by a corresponding relay coil 122. If desired, the pump 48 may be driven by a three-phase motor, in which event each of the switches 116 and 118 may be connected to a separate one of the three-phase supply lines; however, in the preferred form single phase AC is supplied to the motor. The ground side of the pump motor is connected by way of line 124 to the AC ground line 126. Connected across pump motor 48 is a time recorder 128, or hour meter, which records the accumulated time the pump 48 operates.

Energization of pump motor 48' is controlled by coil 122 which, when energized, holds switch contacts 116 and 118 closed. Coil 122 is, in turn, controlled by a main timer 130 which includes a timer motor 132 that is connected directly across the AC lines 120 and 126 by way of lines 134 and 136. The main timer motor 132 drives a pair of movable contacts 138 and 140 to close the respective contacts at the required times during the cycle of operation of the sampler, to be described. Any suitable timer mechanism may be used to operate the switches; for example, a cam 142 driven by the timer motor 132 may be used to open and close the two contacts in the required sequence and at the required intervals. Contact 138, which is shown in a closed position, serves to connect the positive side of the alternating current source from line 134 to the coil 146 of a pump relay 148, the opposite side of coil 146 being connected by way of lines 150 and 152 to line 124, and thence to the ground line 126. Energization of coil 146 closes its corresponding contacts 154 and 156, the closure of contact 156 connecting the AC voltage on line 134 through line 158 to the coil 122, the other side of which is connected through line 160 and lines 152 and 124 to the ground line 126. Accordingly, it will be seen that when the main timer closes contact 138, relay 148 is energized to close contact 156 which, in turn, energizes the pump starter relay 114 to operate the motor 48' for the sampling pump 48.

Energization of the pump relay 148 also serves to close contact 154 which connects the positive voltage on line 134 through line 162 to the "close" input of the motor-driven funnel drain line valve 88. Application of the AC voltage from line 120 through line 162 to valve 88 closes that valve.

The contact 140 in main timer 130 is connected between the AC voltage on line 134 and an output line 164 which leads by way of lines 166 and 168, respectively, to upper and lower float switches 170 and 172 located within the collection tank 22. These two switches are located at selected levels within the tank to control the operation of the system in accordance with the liquid level therein, as will be described.

When the water level within the tank 22 is above the level of switch 170, that switch remains closed and, when the timer motor operates to close switch 140, current passes through switch 170 to energize a rinse pump relay 174 and a first sequence relay 176. Relay 174 includes a coil 178 which is connected between the float switch 170 and the ground line 126 by way of lines 180, 182 and 184, while relay 176 includes a relay coil 186 which is connected to the float switch 170 by way of lines 180, 188, 190 and 184. When coil 178 is activated, its corresponding switch contact 192 is closed, connecting the drive motor 76' for the rinse pump 76 across the AC source by way of lines 120, 194, relay 174, line 196, line 198 and line 184. Thus, when the timer 130 closes switch contact 140, the rinse pump is activated and remains operative until coil 178 is deenergized by the opening of float switch 170.

The tank drain relay 176 is also energized while contacts 140 and 170 are closed, so that relay coil 186 is energized to close its corresponding switch contacts 200 and 202. The contact 200, when closed, connects AC line 120 through lead 204 to the "open" connection to the electrically actuated valve 88. This is a conventional two position valve which is opened by the application of a voltage to line 204 and is closed by the application of a voltage to line 162. Once opened or closed, the valve remains in that position until the opposite voltage is applied. The common side of the valve motor is connected by way of lines 206, 190 and 184 to the common line 126 of the AC source.

When closed, switch contacts 202 connect the AC line 120 through line 208 to the "open" connection of an electrically operated collection container dump valve 210, which valve is located in a collection tank, dump line 212 (FIG. 1) to empty the collection tank 22, as will be explained. Valve 210 is a two position valve of the type described with respect to valve 88, and includes a common line 214 which is connected by way of lines 190 and 184 to the common AC line 126.

The second float switch 172 is open when the water in tank 22 is above a predetermined level; however, when the water falls below that level, switch 172 closes. When this closure coincides with the closure of timer switch 140, the AC voltage from line 120 is applied through switch 172 and line 216 to the timer motor 218 of a secondary timer 220. Again, this timer is conventional, and may include a suitable cam mechanism such as the cam 222 which operates to close a corresponding secondary timer switch 224 for a preselected length of time. When closed, switch 224 connects the AC line 120 to a transfer relay 226 and to a dump valve relay 228 by way of lines 230 and 232, respectively.

The transfer relay 226 includes a relay coil 234 which, when energized by the closure of secondary timer contact 224, shifts its normally closed contact 236 and its normally open contacts 238 and 240. The normally closed contact 236 connects the AC line 120 through line 242 to the "close" connection to the electrically actuated transfer pipe valve 104, thus assuring that this valve is normally closed. When coil 234 is energized, however, the AC line 120 is connected through contact 238 and line 234 to the "open" connection to valve 104, thereby shifting the valve to its open position. The common connection for the valve actuator is connected by way of line 246 to the common AC line 126. When contact 240 is closed by the energization of relay coil 234, AC line 120 is connected by way of lead 248 to the drive motor 94' for the secondary rinse pump 94, the opposite side of the drive motor being connected by way of line 250 to the common AC line 126. Finally, the dump valve relay 228 includes a relay coil 252 which is activated upon closure of switch 224 in the secondary timer to close its corresponding contact 254, thereby connecting the AC line 120 through line 256 to the "close" connection of valve 210. Thus, it will be seen that the secondary timer operates to close contact 224 and thereby open valve 104, activate pump 94 and close valve 210.

The secondary timer motor 218 includes a reset contact which operates, when this motor times out, to produce a reset signal on line 258. This reset signal is applied to the main timer motor 132 to reset it and to start the next operational cycle, and is also applied to a cycle counter 260 which records the total number of reset pulses to provide a readout of the total number of cycles for the main timer.

Figure 4:
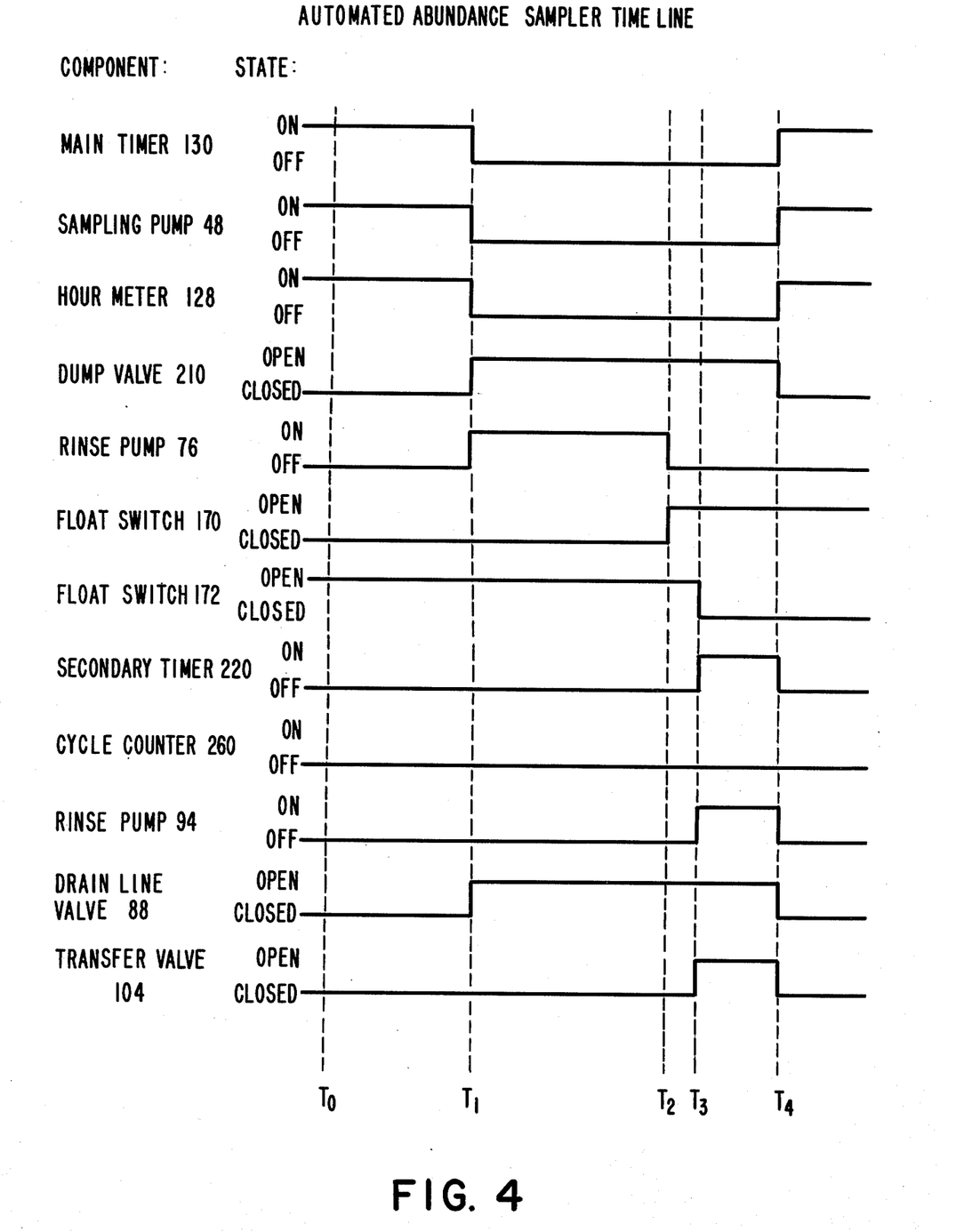
FIG. 4 is a time line diagram for the components of the control system of FIG. 3.

The time line diagram of FIG. 4 shows the relationship of the various elements in the control system and illustrates how the entrainment abundance sampler operates automatically without the need for an attendant while controlling and integrating all of the functions of the various components. In general, the control panel consists of several timers and associated control relays, one of the timers controlling the length of the cycle of the sample pump 48, with the other timer controlling the cycle of the secondary rinse pump.

In operation of the system, the main timer 130 is set to a desired sampling interval, and all of the various pumps and valves are placed in their automatic mode for control by the circuitry of FIG. 3. At the start of a cycle of operation, all of the components are shifted to the condition illustrated at time $T_0$ in FIG. 4, the main timer 130 being "on" to close contact 138 and thereby energize relays 148 and 114 to activate the sample pump 48 and to close the drain line valve 88. At the same time, the transfer valve 104 is held closed, the rinse pumps 76 and 94 are off, the secondary timer is off, and the dump valve 210 is closed.

The sampling pump operates and pumps liquid and entrained ichthyoplankton through the sample inlet pipe 46 to the interior of collection net 30. The water and any solids of less than 500 micron size pass through the net 30 and enter collection tank 22. As the water level rises in tank 22, some flows through discharge line 56 and standpipe 54 into the overflow tank 52. The rising water level in tank 22 first opens the float switch 172, and as it rises further, closes the float switch 170, the water level continuing to rise until it reaches the overflow level defined by the top of the standpipe 54 which is preferably at or near the level of the apex 42 of the collection cone 30. Water flowing out of the standpipe 54 fills the overflow tank 52 to the level of the discharge line 58, the overflow water then passing through this discharge line and through a flow meter 60 to give a measurement of the volume rate of flow and total volume. It will be noted that the liquid and entrained ichthyoplankton enter the collection cone net 30 near its lower portion so that the contact of the ichthyoplankton specimens with the net is reduced as much as possible in order to preserve each specimen intact.

After the selected sampling time has passed, the main timer opens contact 138 at the time $T_1$ indicated in FIG. 4, thereby deenergizing relays 114 and 148 to stop the sampling pump. The main timer then closes contact 140 which allows current to flow through the now-closed float switch 170 to energize the tank drain relay 176 and to open drain line valve 88 and dump valve 210. At the same time, rinse pump relay 174 is energized to activate the rinse pump 76. Accordingly, at time $T_1$, liquid in the collection tank 22 starts to drain both through the dump line 212 and the collection funnel drain line 40.

The flow through the collection funnel drain line 40 carries the specimens collected by net 32 into the lower portion of the secondary collection funnel 82 where the liquid passes up through the 500 micron secondary collection screen 80 and passes out through the secondary collection tank drain line 86. Concurrently, the rinse ring pump 76, which has been started by energization of relay 174, carries rinsing water to the rinse ring 70. This produces a flow of water down the outer surface of collection net 30 to insure that all the specimens that have been collected will flow down to the funnel drain line 40 and that no specimens will stick to the surface of the collection net.

When the water level in collection tank 22 falls to the level of the higher float switch 170 at time $T_2$ in FIG. 4, float switch 170 opens to deenergize the rinse pump relay 174 and the tank drain relay 176. This turns off the rinse pump 76, but has no effect on the valves 88 and 210, so the tank 22 continues to drain. When the level of the water falls to the height of the lower float switch 172, that switch closes to energize the secondary timer 220 which closes switch contact 224 for a preselected period of time. This occurs at time $T_3$ in the time chart of FIG. 4, and serves to energize the transfer relay 226 and the dump valve relay 228, causing the secondary rinse pump 94 to be energized, opening the specimen transfer line valve 104 and closing the collection tank dump valve 210. The specimens that have been transferred from the main collection net 30 to the secondary collection funnel 82 are now washed from and drain out of the secondary collection funnel into the specimen receiving container 100.

The secondary rinse pump 94 continues to operate for a preset period of time as determined by the secondary timer 220 to insure that all the specimens are transferred from the secondary collection funnel 82 to the specimen receiving container 100. When the timer for the secondary rinse pump 94 times out, it produces a reset pulse which resets the main timer 130 and at the same time opens contact 224 to denergize pump 94 and close valve 104. This timing out of the secondary timer 220 occurs at time T₄ and serves to return the system to its original condition condition so that the sampling cycle can start again. The resetting of the main timer closes its contact 138 to start the sample pump 48 and to close valve 88, allowing a second sampling of water and specimens to be transferred into the tank 22.

The specimens and liquid which are transferred to the specimen receiving container 100 are further separated as the liquid is allowed to flow out through drain line 106, which is also provided with a 500 micron screen. The drain line 106 is placed in the specimen container 100 so that it will not be blocked either by the specimens or by detritus. The specimen container may then be removed either manually or automatically from the transfer pipe 102 and replaced by a new specimen container to receive specimens collected in the subsequent cycle of the sampler.

While there has hereinabove been fully and completely described a preferred embodiment of an automated entrainment abundance sampler in accordance with the present invention, it will be obvious to one of skill in the art that a number of changes could be made without departing from the true spirit and scope of the invention. For example, the lengths of operation of the sampling pump and the several rinse pumps can be varied in response to specimen abundance and detrital load. The length of the valve openings and hence the drain time of the collection tank can be varied. A slower drain of the collection tank provides a longer rinse time for the collection net 30. Similarly, the length of time that the secondary rinse pump operates can also be varied. The screen mesh size should be the same for the collection net 30, the secondary collection screen 80 and the screen 108 in the specimen container drain line 106. However, various sizes of screen can be used as desired. Further, the materials used for the various containers, pipes, valves and any other wetted surfaces can be varied so long as the material is not harmful to the ichthyoplankton being collected. The specific components of the control panel can also be varied so long as the controls are able to operate the system as described above. Accordingly, the invention is to be limited only by the following claims.

We claim:

1. An automated entrainment abundance sampler for use in separating specimens from water in which they are contained and for collecting said specimens, said sampler comprising:
   a collection net positioned within a collection tank, said collection net receiving said specimens and water;
   means for transferring said specimens from said collection net to a secondary concentrator for further concentrating said specimens separated from the water by said collection net;
   means for transferring said specimens from said secondary concentrator to a specimen receiving container for storage of said specimens;
   means for rinsing said collection net and said secondary concentrator to facilitate complete transfer of said specimens to said specimen receiving container; and
   means for controlling said sampler whereby said specimens are separated from the water and stored automatically.

2. The sampler of claim 1 wherein said collection net is an inverted mesh cone.

3. The sampler of claim 2 further including a collection funnel upon which said inverted mesh cone is positioned.

4. The sampler of claim 2 wherein said specimens and water are discharged into said cone adjacent a base portion of said cone.

5. The sampler of claim 1 further including means to maintain the water in said collection tank at a desired level.

6. The sampler of claim 5 wherein said means to maintain said desired water level is an overflow tank having an overflow stand pipe which receives water from said collection tank.

7. The sampler of claim 1 wherein said secondary concentrator includes a secondary screen secured within a secondary collection funnel.

8. The sampler of claim 7 wherein said secondary collection funnel is positioned within a secondary collection tank.

9. The sampler of claim 1 further including a refrigerated housing for said specimen receiving container.

10. The sampler of claim 2 wherein said means for rinsing said mesh cone includes a rinse ring having nozzles, said rinse ring being positioned within said collection tank adjacent an upper portion of said inverted mesh cone.

11. The sampler of claim 10 further including a rinse ring pump for pumping water to said rinse ring.

12. The sampler of claim 7 wherein said means for rinsing said secondary concentrator includes a secondary screen rinse line which terminates at a secondary rinse nozzle positioned within said secondary collection funnel.

13. The sampler of claim 12 further including a secondary rinse pump for puming water to said secondary rinse nozzle.

14. An automated entrainment abundance sampler for separating specimens from water and for collecting said specimens, said sampler comprising:
   an inverted, conical collection net positioned in a collection tank, said net receiving the water and specimens to be separated, the water passing through the net while said specimens are retained within said net;
   means for controlling the level of the water in said collection tank;
   a secondary concentrator in fluid communication with the interior of said net, said secondary concentrator receiving said separated specimens from said net and further concentrating said specimens;
   a specimen receiving container positioned in a housing, said specimen receiving container receiving said specimens from said secondary concentrator;
   means for rinsing said inverted conical net and said secondary concentrator to rinse all of said specimens to said specimen receiving container; and
   means for automatically controlling the supply of said specimens to said conical net, the transfer of said specimens to said secondary concentrator and said specimen receiving container and the operation of said rinse means whereby said sampler will automatically separate said specimens from the water and concentrate and collect said specimens.

15. A method of automatically separating specimens from water and for collecting said separated specimens, said method including the steps of:

pumping said water and specimens into the interior of a net positioned within a collection tank;

transferring the water out of said collection tank while retaining said specimens in said net;

stopping pumping of said water and specimens and transferring said specimens from said net to a secondary concentrator for further concentration;

rinsing said net and said secondary concentrator to completely transfer said specimens to a specimen receiving container; and automatically controlling said pumping of said water and specimens to said net, said transfer of said specimens to said secondary concentrator and said specimen receiving container and said rinsing of said net and said secondary concentrator whereby said specimens are automatically separated from the water and retained in said specimen receiving container.

* * * * *